United States Patent [19]

Kurosawa et al.

[11] Patent Number: 4,938,861
[45] Date of Patent: Jul. 3, 1990

[54] LIMITING CURRENT-TYPE OXYGEN SENSOR

[75] Inventors: Hideyuki Kurosawa; Kazuhiro Takahashi; Tetsuo Uchiyama; Yukio Nakanouchi, all of Kumagaya, Japan

[73] Assignee: Kabushiki Kaisha Riken, Tokyo, Japan

[21] Appl. No.: 388,605

[22] Filed: Aug. 1, 1989

[51] Int. Cl.$^5$ .............................................. G01N 27/41
[52] U.S. Cl. .................................................... 204/425
[58] Field of Search .................. 204/425, 410, 412, 1 S

[56] References Cited

U.S. PATENT DOCUMENTS

| 4,666,566 | 5/1987 | Mizutani et al. | 204/1 T |
| 4,772,376 | 9/1988 | Yukawa et al. | 204/410 |
| 4,795,544 | 1/1989 | Nishizawa et al. | 204/425 |
| 4,798,693 | 1/1989 | Mase et al. | 264/44 |

FOREIGN PATENT DOCUMENTS

| 57-48648 | 3/1982 | Japan . |
| 57-97439 | 6/1982 | Japan . |
| 58-210560 | 12/1983 | Japan . |
| 59-88653 | 5/1984 | Japan . |
| 59-26895 | 7/1984 | Japan . |
| 60-24445 | 2/1985 | Japan . |

*Primary Examiner*—G. L. Kaplan
*Attorney, Agent, or Firm*—Brumbaugh, Graves, Donohue & Raymond

[57] ABSTRACT

A limiting current-type oxygen sensor including (a) an oxygen ion-permeable substrate made of a zirconia solid electrolyte having a gas diffusion pore extending between first and second surfaces of the substrate for rate determination by oxygen diffusion through the pore; (b) a first porous electrode formed on the first surface of the substrate in an area including an opening of the gas diffusion pore; (c) a second porous electrode formed on the second surface of the substrate such that it is opposite to the first porous electrode via the substrate; (d) a sealing member fixed to the second surface of the substrate for sealing the second porous electrode such that the internal chamber is defined on the second porous electrode; and (e) a heating means mounted to the sealing member.

4 Claims, 5 Drawing Sheets

LIMITING CURRENT-TYPE OXYGEN SENSOR

BACKGROUND OF THE INVENTION

The present invention relates to a limiting oxygen sensor utilizing a zirconia solid electrolyte as an oxygen ion-permeable solid medium, and more particularly to an oxygen sensor suitable for detecting an oxygen-depleted state in a relatively low temperature environment, particularly in working environment such as construction sites, in tanks, etc.

As miniature, high-sensitivity oxygen sensors, limiting current-type oxygen sensors utilizing a zirconia solid electrolyte as an oxygen ion-permeable means have conventionally been known.

The zirconia solid electrolyte is, as is well known, a ceramic of $ZrO_2$ (zirconia) containing CaO (calcia) or $Y_2O_3$ (yttria) , etc. as a stabilizer in the form of a solid solution. This zirconia solid electrolyte shows a high oxygen ion permeability at a constant voltage when heated to 350° C. or higher. In other words, in an atmosphere containing oxygen, the zirconia solid electrolyte can selectively permit oxygen to pass therethrough. This solid electrolyte-type sensor can detect oxygen concentration in a gas being measured, by utilizing peculiar characteristics of such solid electrolyte.

In addition, the zirconia solid electrolyte has excellent heat resistance, corrosion resistance, thermal shock resistance, etc. Utilizing such advantages, the oxygen sensor made of a zirconia solid electrolyte is widely used for controlling combustion in boilers and furnaces, controlling air-fuel ratios and setting optimum conditions for cleaning exhaust gas in internal engines of automobiles, etc. and further detecting an oxygen-depleted state in such working environments as construction sites, in tanks, etc.

Solid electrolyte-type sensors utilized in such wide applications are generally classified into an oxygen concentration cell-type and an electrochemical pumping-type.

The oxygen concentration cell-type sensor generally has a structure in which a substrate made of a zirconia solid electrolyte is provided with porous Pt electrodes on both surfaces thereof. One electrode is in contact with a gas being measured while the other electrode is in contact with a reference gas having a known oxygen concentration, for instance, the air. By this structure, an oxygen concentration cell is formed, and the measurement of electromotive force of this oxygen concentration cell can lead to the detection of the oxygen concentration of the gas being measured.

On the other hand, the electrochemical pumping-type sensor is constructed such that the oxygen concentration of the gas being measured can be detected by utilizing an electrochemical pumping function. This electrochemical pumping function means that when voltage is applied to an oxygen ion-permeable zirconia solid electrolyte, the oxygen in the gas being measured is reduced to oxygen ions by a negative electrode, and these oxygen ions move through the solid electrolyte to a positive electrode, where they are oxidized to oxygen again, and it is discharged outside.

As a typical sensor utilizing the above electrochemical pumping function, a limiting current-type oxygen sensor is disclosed in Japanese Patent Publication No. 59-26895. This limiting current-type oxygen sensor will be explained as a first type sensor referring to FIG. 7.

In FIG. 7, the sensor comprises a planar oxygen ion-permeable solid electrolyte 21 provided with a porous internal electrode (negative electrode) 22 and a porous external electrode (positive electrode) 23 on both surfaces thereof. Fixed to the solid electrolyte 21 on the side of the internal electrode 22 is a gas diffusion adapter 24 provided with a gas diffusion pore 25 having a desired pore diameter for permitting an oxygen gas to go into an internal chamber 26 defined by the solid electrolyte 21 and the gas diffusion adapter 24. 27 denotes a DC power supply, and 28 denotes a current measurement circuit, one terminal of which is connected to a positive terminal of the DC power supply 27. 29 denotes a lead wire for connecting the internal electrode 22 to the negative terminal of the DC power supply 27, and 30 denotes a lead wire for connecting the external electrode 23 to the current measurement circuit 28.

In the limiting current-type oxygen sensor having the above structure, when a certain voltage is applied to the solid electrolyte 21 by the DC power supply 27 with the internal electrode 22 and the external electrode 23 biased negatively and positively, respectively, oxygen in the internal chamber 26 is electrochemically pumped to the outside through the solid electrolyte 21. In this process, the amount of oxygen diffused through the gas diffusion pore 25 from outside into the internal chamber 26 is controlled by the rate of oxygen diffusion through the gas diffusion pore 25, so that the amount of oxygen ions moving in the solid electrolyte 21 is kept constant. As a result, a constant limiting current proportional to the oxygen concentration in the gas being measured flows in the electric current measurement circuit 28. Thus, the oxygen concentration in the gas being measured can be known from the limiting current obtained by applying a constant voltage.

The limiting current obtained in such a process varies depending upon the size of the gas diffusion pore 25, namely an opening ratio (an area of opening / length of pore) of the gas diffusion pore 25. When the opening ratio is decreased by decreasing the pore diameter of the gas diffusion pore 25, the rate of the process is more controlled by oxygen diffusion through the gas diffusion pore 25, leading to the decrease in limiting current.

On the other hand, when the opening ratio is increased by increasing the pore diameter of the gas diffusion pore 25, the rate of process is less controlled by oxygen diffusion through the gas diffusion pore 25, leading to the increase in a limiting current. Apart from the influence by the area of the electrode, it is generally satisfied that the smaller the limiting current, the smaller the voltage applied to obtain such limiting current.

Japanese Patent Laid-Open No. 59-88653 discloses as a second type a limiting current-type oxygen sensor as shown in FIG. 8.

In FIG. 8, the oxygen sensor comprises a tubular oxygen ion-permeable solid electrolyte container ($ZrO_2 + Y_2O_3$) 32 provided with a gas diffusion pore 33 in a center portion of the bottom of the container 32. This solid electrolyte container 32 is provided, on both upper inner and outer surfaces, with a negative electrode 34 and a positive electrode 35. A top opening portion of the container 32 is lined with a metallized layer 36. 37 denotes an elongated lid member made of the same material as that of the container 32, an upper side wall of which is coated with a metallized layer 38. The solid electrolyte container 32 and the lid member 37 are in contact with each other between the metallized layers 36 and 38 via an annular seal member 39.

In this oxygen sensor of the second type, oxygen in a gas being measured is diffused from outside (a system to be measured) to a cavity defined by the solid electrolyte container 32 and the lid member 37 via the gas diffusion pore 33, and oxygen diffusion through the gas diffusion pore 33 determines a total oxygen diffusion rate of this sensor. Accordingly, a constant limiting current in proportion to the oxygen concentration of the gas being measured flows between the negative electrode 34 and the positive electrode 35, thereby enabling the detection of oxygen concentration.

Further, a limiting current-type oxygen sensor is known by Japanese Patent Laid-Open No. 57-48648.

In addition to the above limiting current-type oxygen sensors, oxygen sensors having electrochemical pumping mechanisms and oxygen concentration detection elements are also known.

Japanese Patent Laid-Open No. 57-97439 discloses as a third type an oxygen sensor shown in FIG. 9.

In FIG. 9, the oxygen sensor comprises an oxygen pumping element 45 constituted by a solid electrolyte 41 having a fine pore 44 substantially in a center thereof and electrodes 42, 43 formed on both surfaces of the solid electrolyte 41, and an oxygen detection element (oxygen concentration cell) 49 constituted by a solid electrolyte 46 and electrodes 47, 48 formed on both surfaces of the solid electrolyte 46. The oxygen pumping element 45 and the oxygen detection element 49 are fixed to each other via an annular conductive member 50 such that their planar surfaces are opposite to each other. An internal chamber 51 is defined by the electrodes 43, 48 and the annular conductive member 50. 52 denotes a DC power supply, 53 denotes an electromotive force meter and 54-57 denote lead wires. Incidentally, contact portions of the oxygen pumping element 45 and the oxygen detection element 49 may be sealed with a glass material.

When a constant voltage is applied to the oxygen pumping element 45 by the DC power supply 52, the internal chamber 51 is filled with a reference gas (air) by an oxygen pumping function. In this state, when the electrode 47 of the oxygen detection element 49 is brought into contact with a gas to be measured, an oxygen concentration cell is formed, whereby an electromotive force in proportion to a ratio of the oxygen concentration of the reference gas to the oxygen concentration of the gas being measured can be obtained from the element 49. The oxygen concentration of the gas being measured can be known by measuring this electromotive force by an electromotive force meter 53.

Japanese Patent Laid-Open No. 58-210560 discloses as a fourth type an oxygen sensor which has a similar structure to that shown in FIG. 8. Namely, the oxygen sensor of the fourth type comprises a tubular oxygen ion-permeable ceramic element provided with a gas diffusion pore in its bottom and two pairs of electrodes opposite to each other via the gas diffusion pore on both inner and outer surfaces of the bottom, and a ceramic lid member for sealing an open end of the tubular oxygen ion-permeable ceramic element, thereby providing an internal chamber therebetween. One pair of electrodes and a ceramic element portion therebetween function as a pumping cell, and another pair of electrodes and a ceramic element portion therebetween function as a sensor cell (oxygen concentration cell). The principle of oxygen concentration detection in the oxygen sensor of the fourth type is essentially the same as in that of the third type.

Japanese Patent Laid-Open No. 60-24445 discloses as a fifth type an automobile oxygen sensor as shown in FIG. 10.

In FIG. 10, the oxygen sensor comprises a cylindrical ceramic member 61 and a lean sensor (limiting current-type oxygen sensor capable of detecting oxygen only in a lean range of an air-fuel ratio) 65 attached to one open end of the cylindrical member 61. The lean sensor 65 is constituted by an oxygen ion-permeable solid electrolyte 62 having a gas diffusion pore 64 in its center, and electrodes 63a, 63b formed on both surfaces of the solid electrolyte 62. The oxygen sensor also comprises an oxygen pump 68 fixed in the cylindrical member 61 such that an internal chamber is defined between the lean sensor 65 and the oxygen pump 68. The oxygen pump 68 is constituted by an oxygen ion-permeable solid electrolyte 66 and electrodes 67a, 67b formed on both surfaces of the solid electrolyte 66. 69a and 69b denote lead wires, 70 and 72 denote stabilized DC power supplies, 71 denotes a current measurement circuit, and 73 denotes a heater contained in the cylindrical member 61.

In this oxygen sensor of the fifth type having the above structure, the internal chamber is filled with oxygen having a known concentration pumped by the oxygen pump 68, and a gas introduced through the gas diffusion pore 64. Accordingly, even when the gas being measured is in a rich state of an air-fuel ratio (oxygen-depleted state), the internal chamber is in a lean state (oxygen excess state). Therefore, a limiting current obtained by the lean sensor 65 can lead to the detection of oxygen concentration in the gas being measured.

However, the above-described solid electrolyte-type oxygen sensors have various problems as mentioned below.

In the case of the oxygen concentration cell-type sensor, since the reference gas is required as its essential element, the sensor volume is inevitably large, consuming much electric energy.

In the cases of the electrochemical pumping-type sensors exemplified by the first and second types, the reference gas is not needed, making it possible to miniaturize the sensor itself as compared to the above-described oxygen concentration cell-type sensor. However, it still suffers from the following peculiar problems. That is, to achieve the rate determination by oxygen diffusion, the adapter 24 having a gas diffusion pore 25 is needed as an additional element in the first type, and the lid member 37 and the seal member 39 are needed in the second type. Accordingly, these electrochemical pumping-type sensors have relatively complicated structures because of increased numbers of parts.

In the cases of the oxygen sensors having the electrochemical pump and the oxygen concentration cell exemplified by the third and fourth types, and the oxygen sensor of the fifth type having the electrochemical pump and the lean sensor, they are disadvantageous in complicated structure. In addition, constituent elements such as the electrochemical pump, the oxygen concentration cell and the lean sensor should be quality-controlled, but the control of their quality is rather difficult. As a result, unevenness in quality inevitably occurs among the sensors having such elements.

Also, in the above-described electrochemical pumping-type sensors, to increase response velocities by decreasing the heat capacities of the overall sensors, the sensors themselves should be miniaturized. In this case, the gas diffusion pores inevitably have reduced diameters in the above structures. However, in the electrochemical pumping-type sensors, the gas diffusion pores are directly exposed to a gas being measured. Accordingly, the fine diffusion pores are likely to be clogged with dust in the gas being measured, leading to the deterioration of their function as sensors.

Further, in the conventional oxygen sensors, a heating means is necessary to obtain a desired output current. However, in the oxygen sensor of the first type, a heating means which is desired to be mounted to the gas diffusion adapter 24 does not show high heating efficiency, because the adapter 24 cannot be made extremely thin. In the oxygen sensors of the second and third types, there is no proper space for mounting the heating means. In the oxygen sensor of the fifth type, since a heater 73 is embedded in the cylindrical member 61, sealed portions may not be completely tight because of thermal expansion.

OBJECT AND SUMMARY OF THE INVENTION

An object of the present invention is, therefore, to provide a limiting current-type oxygen sensor having a structure suitable for miniaturization, which is excellent in stability and enjoys a long service life.

The present invention provides the limiting current-type oxygen sensor comprising (a) an oxygen ion-permeable substrate made of a zirconia solid electrolyte and having a gas diffusion pore extending between first and second surfaces of the substrate for rate determination by oxygen diffusion through the pore; (b) a first porous electrode formed on the first surface of the substrate in an area including an opening of the gas diffusion pore; (c) a second porous electrode formed on the second surface of the substrate such that it is opposite to the first porous electrode via the substrate; (d) a sealing member fixed to the second surface of the substrate for sealing the second porous electrode such that an internal chamber is defined on the second porous electrode; and (e) a heating means mounted to the sealing member.

DETAILED DESCRIPTION OF THE INVENTION

Figure 1:
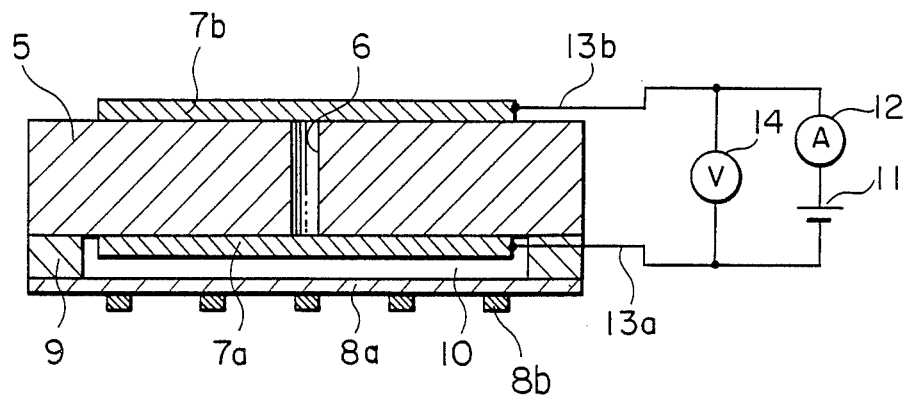
FIG. 1 is a cross-sectional view showing the oxygen sensor according to one embodiment of the present invention.

Referring to FIG. 1, the oxygen sensor according to one embodiment of the present invention comprises an oxygen ion-permeable, planar substrate 5 made of a zirconia solid electrolyte and provided with a gas diffusion pore 6 substantially in its center portion for rate determination by oxygen diffusion.

The zirconia solid electrolyte constituting the substrate 5 is, for instance, made of $ZrO_2$ in which at least one of $Y_2O_3$, $MgO$, $Yb_2O_3$, etc. is dissolved as a stabilizer. In FIG. 1, only one diffusion pore 6 is provided in the substrate 5, but a plurality of diffusion pores may be provided.

To achieve the miniaturization of the oxygen sensor and the operation of the oxygen sensor at a low temperature, particularly at 350°–500° C., the substrate 5 preferably has a thickness of 0.1–0.5 mm and the diffusion pore 6 preferably has a pore diameter of 10–30 μm.

On inner and outer surfaces of the substrate 5, a porous internal electrode (negative electrode) 7a, and a porous external electrode (positive electrode) 7b are provided in areas opposite to each other via the substrate 5, which include the opening of the diffusion pore 6 and recede from the periphery of the substrate 5 with a predetermined width.

Incidentally, the internal electrode 7a, which is not directly exposed to a gas to be measured, and so is less likely to be affected by dust, may be located such that it does not cover an opening of the diffusion pore 6.

Since the internal and external electrodes 7a, 7b function as catalytically active electrodes, they are preferably made of metal materials such as Pt, Pd, Ag, Rh, Ir, etc. or mixed materials of these metal materials and at least one oxygen ion-permeable oxide material, and particularly Pt or a mixed material of Pt and $ZrO_2$ is preferable.

These electrodes 7a, 7b should be porous. In this case, the electrodes preferably have an average particle size of 1–3 μm and an average pore size of 0.1–5 μm and a porosity of 70–85%.

In a case where these factors are within the above ranges, the electrodes 7a, 7b function as filters for dust contained in a gas being measured. Because of this function, an effective diameter of the diffusion pore 6 does not change, and the rate-determining function of the diffusion pore 6 can be maintained.

The internal electrode 7a is sealed such that an internal chamber 10 is provided thereon. For instance, in the case of FIG. 1, a sealing plate 8a is fixed to the substrate 5 via an annular sealing spacer 9 in a peripheral area of the inner surface of the substrate 5 to define the internal chamber 10. To minimize the heat capacity of the oxygen sensor itself, it is preferable that the internal chamber 10 has a small volume and that the sealing plate 8a is a thin ceramic plate or a thin ceramic cap made of $ZrO_2$, etc. having a small heat capacity. Incidentally, the sealing spacer 9 is preferably made of glass materials to substantially isolate the internal chamber 10 from the outside atmosphere.

A heating means 8b is mounted to the sealing plate 8a on an opposite side to the internal chamber 10. This heating means 8b functions to heat the sensor to cause the oxygen pumping.

In the oxygen sensor thus constructed according to one embodiment of the present invention, the substrate 5 made of the zirconia solid electrolyte functions as an oxygen ion-permeable medium for effecting oxygen pumping in the operation of the oxygen sensor. And at least one diffusion pore 6 provided in the substrate 5 functions as a means for controlling the rate of oxygen supply from the outside (a gas to be measured) to the internal chamber 10. Namely, the overall oxygen supply rate is determined by the rate of oxygen diffusion through the diffusion pore 6.

In the oxygen sensor of the present invention, part of oxygen in the internal chamber 10 escapes through the external electrode 7b, but the amount of oxygen escaped is negligible in an atmosphere in which the oxygen concentration is several percents.

Since the sealing members such as the sealing plate 8a and the sealing spacer 9 are fixed to the substrate 5 such that the internal electrode 7a is sealed and the internal chamber 10 is defined, the atmosphere in this internal chamber 10 is substantially isolated from the gas atmosphere being measured.

A limiting current flowing through a current measurement circuit 12 is proportional to the oxygen concentration of the gas being measured, by the rate determination by oxygen diffusion through the gas diffusion pore 6. Accordingly, the oxygen concentration can be detected by measuring this limiting current.

The heater 8b is to heat the sensor element to such a temperature that the solid electrolyte shows good ion conductivity (oxygen ion permeability). Since the sealing member can be made thin in the oxygen sensor of the present invention, the solid electrolyte substrate can be efficiently heated.

Accordingly, in the oxygen sensor according to an embodiment shown in FIG. 1, both functions of electrochemical pumping and rate determination by oxygen diffusion necessary for the detection of oxygen concentration can be achieved by a single element.

Further, since the internal and external electrodes 7a, 7b are porous, they function as catalytically active electrodes for activating the electrode reaction, whereby interfaces between the substrate 5, the electrode 7a and oxygen are enlarged, resulting in the increase of oxygen pumping efficiency.

Incidentally, in the embodiment of FIG. 1, since openings of the diffusion pore 6 provided in the substrate 5 are covered by the porous external electrode 7b and the porous internal electrode 7a, the electrodes 7a, 7b function as filters for the diffusion pore 6.

Specific examples of the present invention will be described below in detail.

EXAMPLE 1

In FIG. 1, 5 denotes a substrate made of a zirconia solid electrolyte of $ZrO_2$ (zirconia) containing $Y_2O_3$ (yttria) as a stabilizer. As is well known, when heated to 350° C. or higher in a state where a certain voltage is applied, the zirconia solid electrolyte shows oxygen ion permeability, thereby enabling oxygen pumping.

The substrate made of the zirconia solid electrolyte are both shaped in a dense, planar form with a sufficiently small porosity. In the case of this Example, the thickness of the substrate 5 is 0.5 mm.

6 denotes a diffusion pore provided in the substrate 5 in its center, which extends along the thickness of the substrate 5 with a pore diameter of 15 μm.

The internal and external electrodes 7a, 7b are respectively formed on the inner and outer surfaces of the substrate 5 in areas opposite to each other including both openings of the diffusion pore 6 with a certain space between their peripheries and those of the substrate 5.

These porous internal and external electrodes 7a, 7b function as catalytically active electrodes for activating the function as catalytically active electrodes for activating the electrode reaction. In this Example, they are constituted by Pt electrodes. These Pt electrodes 7a, 7b are formed by coating the substrate 5 in the above areas on its inner and outer surfaces with a conductive paste containing Pt powder having an average particle size of 0.1 μm, an organic binder and an organic solvent and then baking it in the air.

Further, how the Pt electrodes 7a, 7b are porous is determined by various factors such as their average particle size, average pore size and porosity, and these factors are adjusted as follows with full reproducibility:

Average particle size :3 μm
Average pore size :4 μm
Porosity :about 80%

The average pore size of the Pt electrodes 7a, 7b is controlled to be less than the pore diameter (15 μm) of the diffusion pore 6. Accordingly, the Pt electrodes 7a, 7b can function not only as catalytically active electrodes but also as filters for the diffusion pore 6. Specifically speaking, when there is dust such as soot having a particle size larger than the average pore size of the Pt electrodes 7a, 7b, the dust does not clog the diffusion pore 6 because the Pt electrodes 7a, 7b effectively function as filters.

In fact, since the fine pores of the Pt electrodes 7a, 7b are mostly oval in cross section and have pore diameters of submicrons, they can function as filters against dust having a particle size equal to or smaller than the average pore size of the electrodes.

In addition, the Pt electrodes 7a, 7b are as porous as having a porosity of about 80%. Accordingly, even though part of the pores of the Pt electrodes are clogged with dust, sufficient diffusion of oxygen can be maintained through unclogged pores.

The average particle size of the Pt electrodes 7a, 7b are controlled to be fully smaller than the pore diameter (15 μm) of the diffusion pore 6. Accordingly, particles constituting the Pt electrodes 7a, 7b do not directly clog the diffusion pore 6, and so the effective pore diameter of the diffusion pore 6 is kept unchanged. Because of this feature, together with the above porosity of the Pt electrodes 7a, 7b, the rate-determining function of the diffusion pore 6 is not affected by the Pt electrodes.

8a denotes a sealing plate constituted by a thin zirconia plate, and it is fixed to the substrate 5 via an annular sealing spacer 9 made of glass. This sealing spacer 9 can be formed by coating the inner surface of the substrate 5 in an area of a predetermined width outside the Pt electrode 7a with a glass paste.

Because of the above structure, the internal electrode 7a is substantially isolated from the gas atmosphere to be measured by the thin zirconia plate 8a and the sealing spacer 9. As a result, an internal chamber 10 is provided on the internal electrode 7a. This internal chamber 10 has a small thickness and so a small volume.

The external electrode 7b is in direct contact with the gas to be measured while the internal electrode 7a is in contact with the gas being measured which is introduced into the internal chamber 10 through the diffusion pore 6.

11 denotes a stabilized DC power supply, and 12 denotes a current measurement circuit connected in series to a positive terminal of this power supply 11. 14 denotes a voltage measurement circuit connected in parallel to the power supply 11 and the current measurement circuit 12. 13a denotes a lead wire for connecting a negative terminal of the power supply 11 to the internal electrode 7a, and part of the lead wire 13a penetrates through the sealing spacer 9 with full sealing. 13b denotes a lead wire for connecting a terminal of the current measurement circuit 12 to the external electrode 7b.

Since the planar substrate 5 has a gas diffusion pore 6 and since the thin zirconia plate 8a is used to seal the internal electrode 7a, the heat capacity of the oxygen sensor itself is sufficiently small.

Next, the operation of the oxygen sensor of this Example thus constituted will be explained below.

The substrates 5 is heated to a predetermined temperature of 350° C. or higher by the heating means 8b, and in this state, a predetermined voltage is applied between the Pt electrode 7a (negative electrode) and the Pt electrode 7b (positive electrode) by the DC power supply 11.

The oxygen contained in the gas introduced into the internal chamber 10 is discharged through the substrate 5 by an electrochemical oxygen pumping function. Specifically speaking, since the oxygen in the internal chamber 10 is in contact with the porous Pt electrode (negative electrode) 7a, it is reduced to oxygen ions. The oxygen ions move through the biased substrate 5 to reach the porous Pt electrode (positive electrode) 7b, where they are oxidized to an oxygen gas. The oxygen gas thus formed escapes outside through the porous Pt electrode 7b.

Once oxygen pumping takes place like this, the oxygen concentration in the internal chamber 10 decreases, whereby oxygen is supplemented by diffusion through the diffusion pore 6 from the outside gas atmosphere. However, since the diffusion process of oxygen is controlled by the oxygen diffusion through the diffusion pore 6, a constant amount of oxygen escapes from the internal chamber 10 by oxygen pumping. Because of this phenomenon, a constant limiting current i flows through the current measurement circuit 12. This limiting current i is proportional to the oxygen concentration of the gas being measured. Such limiting current characteristics are shown in FIGS. 2 and 3.

Figure 2:
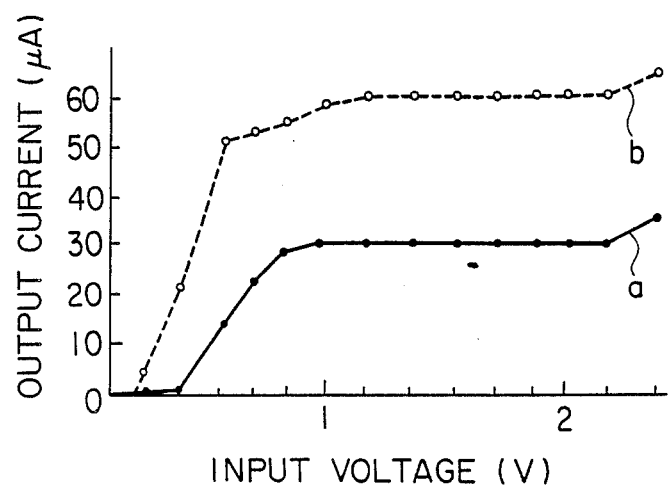
FIG. 2 is a graph showing the relation between output current and input voltage variable with oxygen concentration as a parameter in the oxygen sensor of Example 1.

FIG. 2 shows the dependency of output current on input voltage in the oxygen sensor in this Example. The oxygen sensor is heated at 420° C. In FIG. 2, curves "a" and "b" are characteristic curves when oxygen concentrations are 10% and 21%, respectively.

As is clear from these curves "a" and "b", the higher the oxygen concentration in the gas being measured, the higher output current is obtained from the same input voltage. In both curves "a" and "b", at input voltage in such a wide range as 1.0-2.2 V, the output current is almost constant, showing no dependency on input voltage. Accordingly, in the cases of oxygen concentrations of 10% and 21%, the limiting current is 30 $\mu$A and 60 $\mu$A, respectively.

Figure 3:
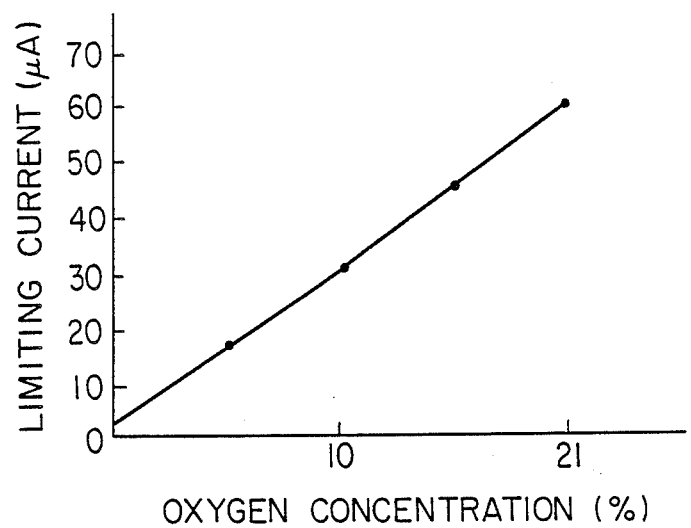
FIG. 3 is a graph showing the relation between the limiting current and the oxygen concentration in the oxygen sensor of Example 1.

FIG. 3 shows the dependency of the limiting current on the oxygen concentration at input voltage of 1.4 V. In this case, too, the substrate 5 is as thick as 0.5 mm, and it is heated at 420° C. It is clear from FIG. 3 that the limiting current changes almost linearly with the oxygen concentration of the gas being measured in a wide range including 0-21%.

EXAMPLE 2

In this Example, the substrate 5 has half a thickness in Example 1, namely 0.25 mm. The diffusion pore 6 has a pore diameter of 15 $\mu$m and a pore length of 0.25 mm.

The porous internal and external electrodes 7a, 7b are formed with a mixture of Pt and $ZrO_2$. The electrodes 7a, 7b are formed by coating the substrate 5 with a conductive paste containing Pt powder having an average particle size of 1 $\mu$m and 8 weight % of $ZrO_2$ powder in a predetermined pattern and then baking it at 300° C.

In this Example, the factors of determining porosities of the electrodes 7a, 7b are controlled to be the following values with full reproducibility.

Average particle size:2 $\mu$m
Average pore size:3 $\mu$m
Porosity:about 70%

As is clear from the above, the electrodes 7a, 7b are fully porous, and as in Example 1, they function not only as catalytically active electrodes but also as filters for the diffusion pore 6.

Figure 4:
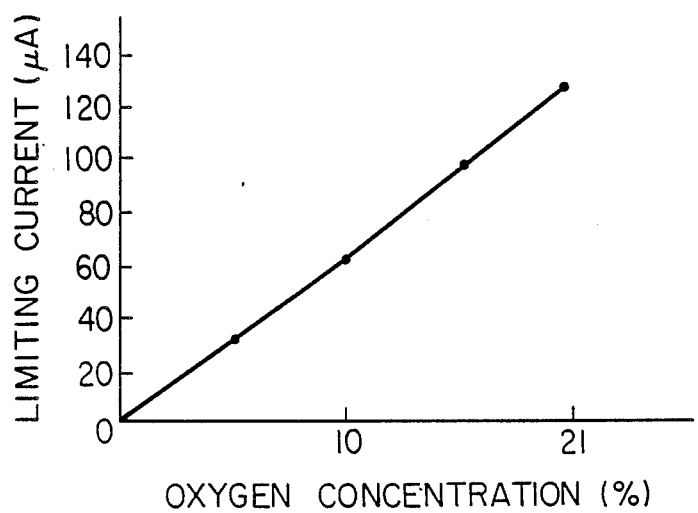
FIG. 4 is a graph showing the relation between the limiting current and the oxygen concentration in the oxygen sensor of Example 2.

FIG. 4 shows the relation between the limiting current and the oxygen concentration in this Example at a heating temperature of 420° C. and an input voltage of 1.4 V.

Figure 5:
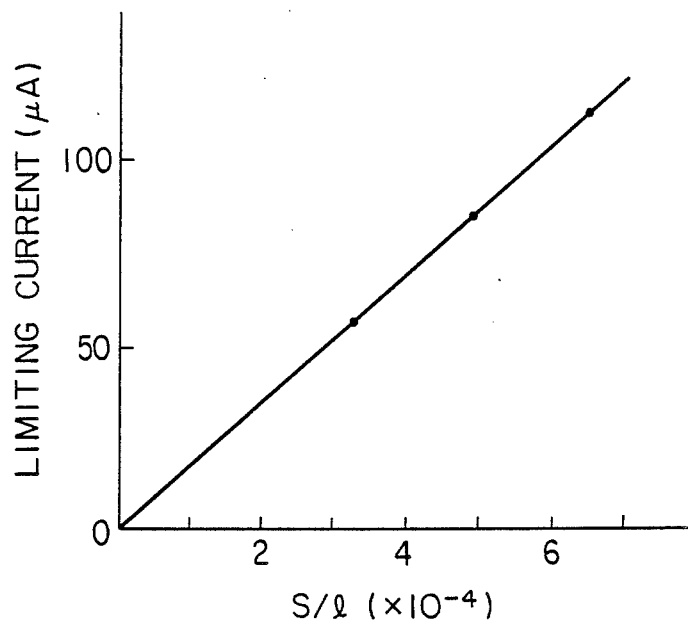
FIG. 5 is a graph showing the relation between the limiting current and the pore diameter (S/l) of the gas diffusion pore.

It is clear from FIG. 5 that the limiting current is proportional to the oxygen concentration of the gas being measured in a wide range including 0-21%. The proportional relation between the limiting current and the oxygen concentration is not affected by the thickness of the substrate 5, the length of the pore size 6, and the types of materials of the electrodes 7a, 7b.

The main factor of determining the limiting current is the diffusion pore 6, oxygen diffusion through which determines the total oxygen supply rate of this sensor. The limiting current can be adjusted by changing the size of the diffusion pore 6.

In Example 2, since the diffusion pore 6 has half a length in Example 1, the total oxygen supply is less controlled by the oxygen diffusion through the diffusion pore 6. As a result, the limiting current is about doubled as compared with the case of FIG. 3.

FIG. 5 shows the dependency of the limiting current on the size of diffusion pore 6. In the diffusion pore 6, its pore length is expressed as "l", and its cross section is expressed as "S". FIG. 5 shows the dependency of limiting current on S/l at an oxygen concentration of 21%.

When S/l is changed in the diffusion pore 6, for instance, when the thickness of the substrate 5, namely the length ("l") of the diffusion pore 6 is changed without changing the pore diameter of the diffusion pore 6, all data vary along the linear line in FIG. 5. This shows that the limiting current is proportional to S/l.

Further, when the rate-determining function is intensified by decreasing a ratio of the cross section area S to the length l in the diffusion pore 6, the limiting current becomes smaller in proportion to the ratio S/l. On the other hand, when the rate-determining function is weakened by decreasing the ratio of the cross section area S to the length l, the limiting current increases in proportion to S/l.

It is confirmed that as long as the electrodes 7a, 7b are fully porous, the rate-determining function of the diffusion pore 6 is not affected by the materials of the electrodes 7a, 7b.

As described above, the substrate (zirconia solid electrolyte) shows oxygen ion permeability when heated to 350° C. or higher, enabling the oxygen pumping of the sensor. Accordingly, when the gas atmosphere to be measured is at 350° C. or higher, the sensor can be operated simply by placing the sensor in this atmosphere.

However, when the temperature of the gas atmosphere to be measured is lower than 350° C., for instance, at room temperature, the sensor should be heated to 350° C. or higher.

Figure 6:
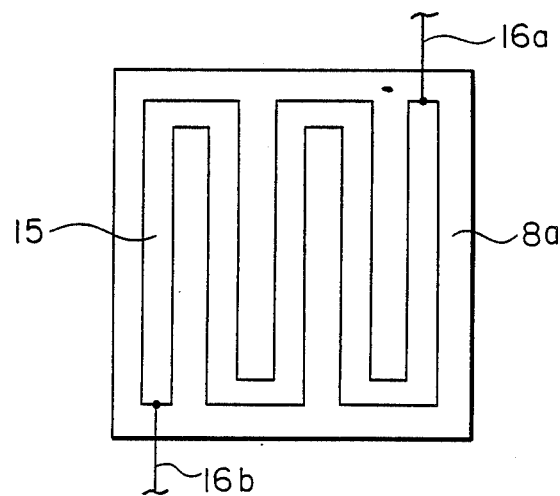
FIG. 6 is a plan view showing a heating means assembled in the oxygen sensor.

A heating means of the sensor will be explained referring to FIG. 6. In FIG. 6, 8a denotes a thin zirconia sealing plate (see FIG. 1) provided with a heater 15 on the opposite side to the internal electrode 7a. With this heating means, the oxygen sensor can be operated even in a gas atmosphere at a relatively low temperature, for instance, at room temperature or lower.

This heater 15 is formed by printing a Pt paste and baking it, and to achieve uniform heating of the sensor, it is formed in a meandering pattern all over the surface of the thin zirconia plate 8a.

Figure 7:
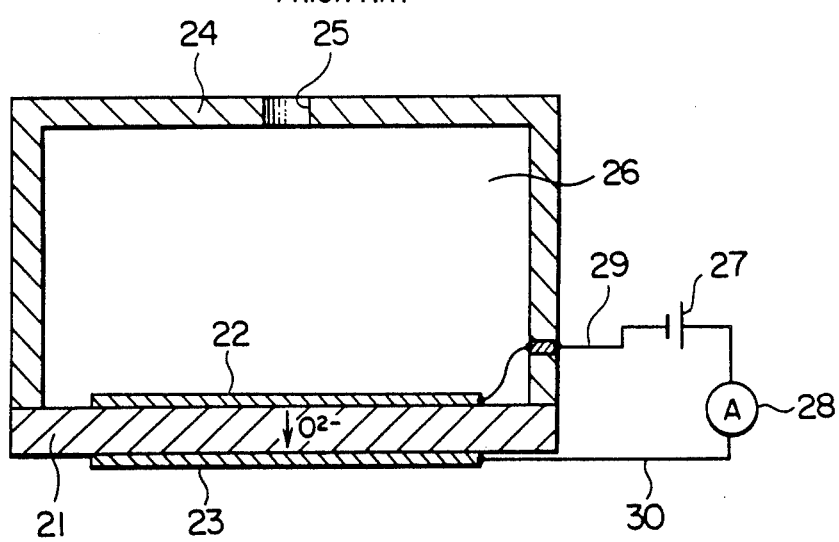
FIG. 7 is a cross-sectional view showing the conventional oxygen sensor of the first type as a limiting current-type oxygen sensor.
Figure 8:
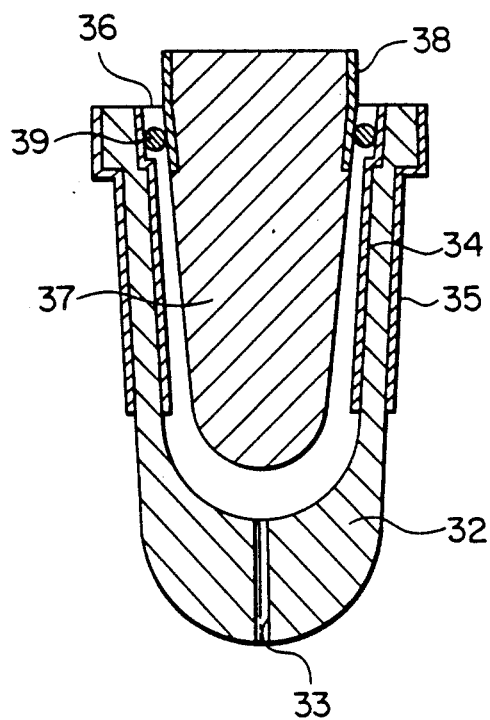
FIG. 8 is a cross-sectional view showing the conventional oxygen sensor of the second type as a limiting current-type oxygen sensor.
Figure 9:
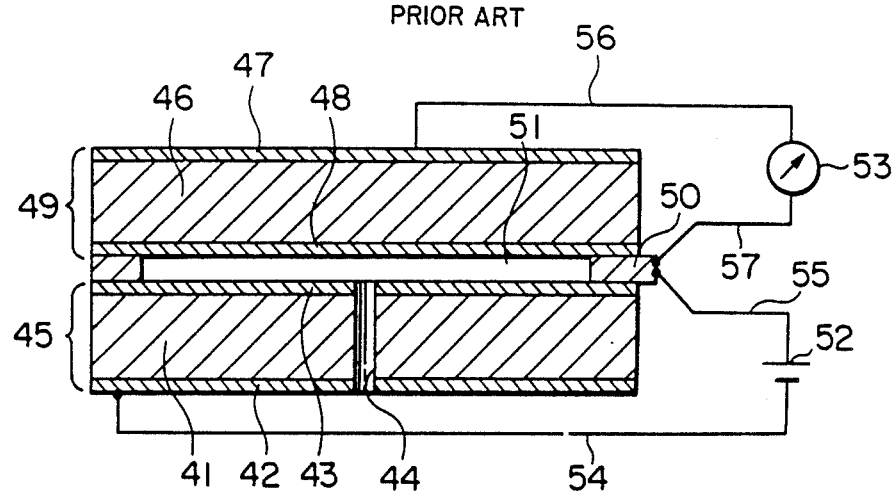
FIG. 9 is a cross-sectional view showing the conventional oxygen sensor of the third type as a limiting current-type oxygen sensor.
Figure 10:
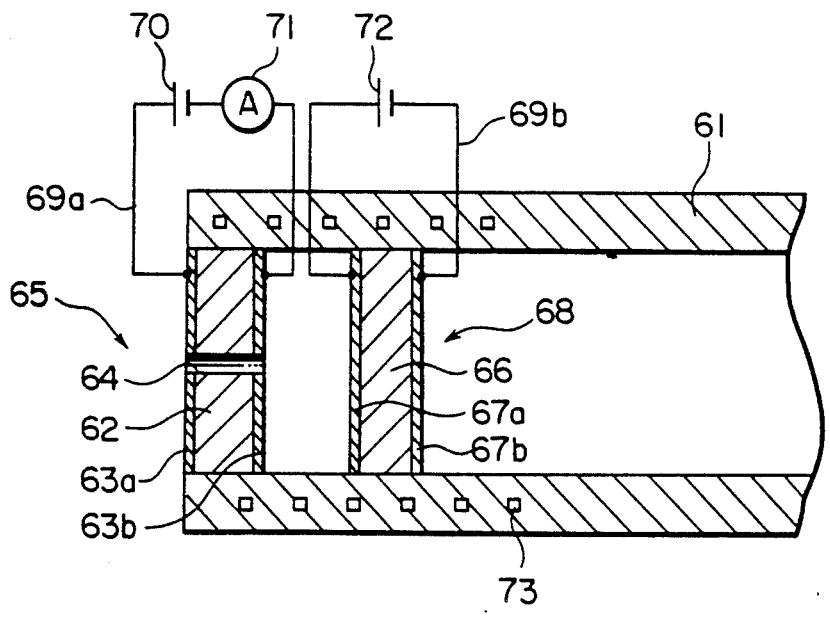
FIG. 10 is a cross-sectional view showing the conventional oxygen sensor of the fifth type as a limiting current-type oxygen sensor.

16a, 16b denote lead wires connected to both terminals of the heater 15. Voltage is applied between the lead wires 16a, 16b to energize the heater 15, so that the substrate 5 can fully function as a solid electrolyte. In this case, since the sensor itself has a small heat capacity, electric energy consumption can be made almost half to achieve a desired heating temperature as compared to the oxygen sensor in which a cap-shaped adapter having diffusion pore of the same size is fixed to the solid electrolyte as a cover (first type shown in FIG. 7).

Incidentally, in the above Examples, the substrate 5 having oxygen ion permeability is formed with a zirconia solid electrolyte prepared by dissolving $Y_2O_3$ as a stabilizer in $ZrO_2$, but the substrate is not restricted to this solid electrolyte. In addition to this zirconia solid electrolyte, such zirconia solid electrolyte made of $ZrO_2$ and containing CaO, MgO, $Yb_2O_3$, etc. as stabilizers may be properly used.

To achieve the miniaturization and low-temperature operation (350°–500° C.) of the oxygen sensor, the substrate 5 preferably has a thickness of 0.1–0.5 mm, and the diffusion pore 6 has a pore diameter of 10–30 μm.

In the above Examples, the substrate 5 has one diffusion pore 6, but the present invention is not restricted to this structure. That is, the substrate 5 may have a plurality of diffusion pores.

In a case where a plurality of diffusion pores are formed, their sizes may be determined to achieve effective rate-determining function, taking into consideration the thickness of the substrate 5, average sizes of the porous internal and external electrodes 7a, 7b and their porosities. In addition, a plurality of diffusion pores 6 may have the same size or different sizes.

Further, in the above Examples, both openings of the diffusion pore 6 in the substrate 5 are covered by the porous internal electrode 7a and the porous external electrode 7b. However, an inner opening of the diffusion pore 6 may not be covered by the first internal electrode 7a, which is not directly exposed to the gas being measured, so that it is less likely to be affected by dust.

The first internal and external electrodes 7a, 7b are not restricted to electrodes made of Pt or Pt and $ZrO_2$. That is, to achieve the function as catalytically active electrodes, metal materials such as Pt, Pb, Ag, Rh, Ir, etc., alloy materials of these elements, or mixed materials of these metal materials and at least one oxygen ion-permeable oxide material may be properly used.

These porous electrodes 7a, 7b may be formed not only by baking of pastes but also by sputtering, vacuum vapor deposition, plating, etc.

In these porous electrodes 7a, 7b, factors of determining their porosities, such as average particle size, average pore size, pore percentage are not restricted to the above values, and they may be determined as follows:

The average pore size of the internal and external electrodes 7a, 7b need only be equal to or smaller than the pore diameter of the diffusion pore 6 in order that the internal and external electrodes 7a, 7b function as filters for the diffusion pore 6. Further, to maintain its rate-determining function without decreasing the effective pore diameter of the diffusion pore 6, the average particle size of the internal and external electrodes 7a, 7b need only be equal to or smaller than the pore diameter of the diffusion pore 6, and the pore percentage of the internal and external electrodes 7a, 7b need only be at such a level that the electrodes themselves do not function as layers for determining the oxygen supply rate.

In sum, in order that the electrodes 7a, 7b can function as filters for the diffusion pore 6, and in order that they can fully function as catalytically active electrodes with large three-phase interfaces between the substrate 5, the electrodes 7a, 7b and oxygen, thereby enhancing their oxygen pumping function, the above factors of the electrodes are preferably within the following ranges:

Average particle size: 1–3 μm
Average pore size: 0.1–5 μm
Porosity: 70–85%

Further, to minimize the heat capacity of the oxygen sensor itself, the internal electrode 7a should be covered by a cover member having a thin bottom plate or a thin, plate, which is made of $ZrO_2$ or other ceramics. The thin plate may be fixed to the substrate 5 via a sealing spacer 9 made of a glass plate, etc.

As described above in detail, the oxygen sensor of the present invention has the following advantages:

(1) Since the electrochemical oxygen pumping function and the rate-determining function are conducted by a single element, the structure of the oxygen sensor can be simplified and low electric energy consumption can be achieved.

(2) As compared with the conventional oxygen sensors in which the oxygen pumping function and the rate-determining function are conducted by separate elements, the oxygen sensor of the present invention can be more easily controlled in its quality, and differences in quality among the products can be minimized.

(3) Since the electrodes are constructed as porous structures, they function as filters for the diffusion pores. This contributes to the improvement of sensor characteristics and the extension of service life of the sensor.

(4) Since the substrate is fully thin, and since the opening ratio (a ratio of the pore diameter of the diffusion pore to the thickness of the substrate) can be made relatively large, the oxygen pumping function and the rate-determining function can be fully maintained even at a low temperature so that the desired limiting current can be obtained. Accordingly, even in a low temperature operation condition, for instance, in working environment such as in tanks, where an oxygen-depleted state is to be detected at a relatively low temperature, a wide range of oxygen concentration can be detected at high accuracy and high response rate.

(5) Since the sealing member can be made thin, the solid electrolyte substrate can be efficiently heated by the heating means.

What is claimed is:

1. A limiting current-type oxygen sensor comprising
 (a) an oxygen ion-permeable substrate made of a zirconia solid electrolyte having a gas diffusion pore extending between first and second surfaces of said substrate for rate determination by oxygen diffusion through said pore;
 (b) a first porous electrode formed on said first surface of said substrate in an area including an opening of said gas diffusion pore;
 (c) a second porous electrode formed on said second surface of said substrate such that it is opposite to said first porous electrode via said substrate;
 (d) a sealing member fixed to said second surface of said substrate for sealing said second porous electrode such that an internal chamber is defined on said second porous electrode;
 (e) a limiting current-detecting means connected between said first and second porous electrodes; and
 (f) a heating means mounted to said sealing member.

2. The limiting current-type oxygen sensor according to claim 1, wherein said substrate has a thickness of 0.1–0.5 mm, and said diffusion pore has a diameter of 10–30 $\mu$m.

3. The limiting current-type oxygen sensor according to claim 2, wherein said internal and external electrodes have an average particle size of 1–3 $\mu$m, an average pore size of 0.1–5 $\mu$m and a porosity of 70–85%.

4. The limiting current-type oxygen sensor according to claim 1, wherein said internal and external electrodes have an average particle size of 1–3 $\mu$m, an average pore size of 0.1–5 $\mu$m and a porosity of 70–85%.

* * * * *